United States Patent [19]
Allegrini et al.

[11] Patent Number: 6,114,523
[45] Date of Patent: Sep. 5, 2000

[54] PROCESS FOR THE RECYCLE OF A WASTE PRODUCT OF DILTIAZEM SYNTHESIS

[75] Inventors: Pietro Allegrini, Lonigo; Gaetano Marchioro, Vicenza; Giuseppe Barreca, Caldiero; Marco Villa; Laura Russo, both of Milan, all of Italy

[73] Assignee: Zamon Group S.p.A., Vicenza, Italy

[21] Appl. No.: 09/176,189

[22] Filed: Oct. 21, 1998

[30] Foreign Application Priority Data

Oct. 22, 1997 [IT] Italy .................. MI97A2374

[51] Int. Cl.$^7$ ...................... C07C 323/62; C07D 281/10
[52] U.S. Cl. .................... 540/491; 560/17; 562/401; 562/431
[58] Field of Search ............ 540/491; 560/17; 561/401, 431

[56] References Cited

U.S. PATENT DOCUMENTS

| | | | |
|---|---|---|---|
| 5,097,059 | 3/1992 | Giordano et al. | 560/17 |
| 5,102,999 | 4/1992 | Giordano et al. | 540/491 |
| 5,144,025 | 9/1992 | Tentorio | 540/491 |
| 5,223,612 | 6/1993 | Giordano et al. | 540/491 |

FOREIGN PATENT DOCUMENTS

| | | |
|---|---|---|
| 0 059 335 | 9/1982 | European Pat. Off. . |
| 0 098 892 | 1/1984 | European Pat. Off. . |
| 0 395 323 | 10/1990 | European Pat. Off. . |
| 0 447 135 B1 | 9/1991 | European Pat. Off. . |
| 0 450 705 A1 | 10/1991 | European Pat. Off. . |
| 0 617 130 A2 | 9/1994 | European Pat. Off. . |
| 71 08 982 | 3/1971 | Japan . |
| 1236467 | 6/1971 | United Kingdom . |
| 2 130 578 | 6/1984 | United Kingdom . |

OTHER PUBLICATIONS

MERK Index Citation 3247 Dilitiazem, 12$^{TH}$ Ed., 1996.

Yamada et al, Asymmetric Reduction of a 1,5–Benzothiazepine Deriviative with Sodium Borohydride–(S)–alphaAmino Acids: An Efficient Synthesis of a Key Intermediate of Diltiazem J. Org Chem 1996, 61 8586–8590.

*Primary Examiner*—Richard L. Raymond
*Attorney, Agent, or Firm*—Arent Fox Kintner Plotkin & Kahn

[57] ABSTRACT

A process which allows the re-use of compounds of formula

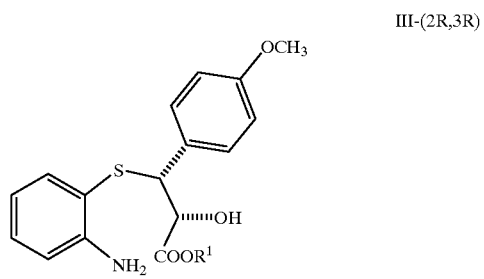

in diltiazem synthesis through a process of conversion to a mixture of enantiomers III-(2R,3R) and III-(2S,3S) is described.

9 Claims, No Drawings

PROCESS FOR THE RECYCLE OF A WASTE PRODUCT OF DILTIAZEM SYNTHESIS

The present invention relates to a method for the recycle of a waste product of diltiazem synthesis and, more particularly, it relates to a method for the preparation of threo-2-hydroxy-3-(2-aminophenylthio)-3-(4-methoxyphenyl)propionic acid esters, intermediates useful for the synthesis of diltiazem, starting from (2R,3R)-2-hydroxy-3-(2-aminophenylthio)-3-(4-methoxyphenyl) propionic acid or derivatives thereof.

Diltiazem, (+)-(2S,3S)-3-acetoxy-5-[2-(dimethylamino) ethyl]-2,3-dihydro-2-(4-methoxy-phenyl)-1,5-benzothiazepin-4(5H)-one (The Merck Index, XII ed., no. 3247, page 541) is a known drug with calcium-antagonist activity described in the U.K. patent 1236467 (Tanabe Seiyaku Co. Ltd.).

Several methods for the preparation of diltiazem such as, for example, those described in the above cited U.K. patent 1236467, in the European patent application 0 059 335 and in the Japanese patent no. 71/8982, all in the name of Tanabe Seiyaku Co. Ltd., are described in the literature.

Most of these methods substantially provide for the following synthetic scheme.

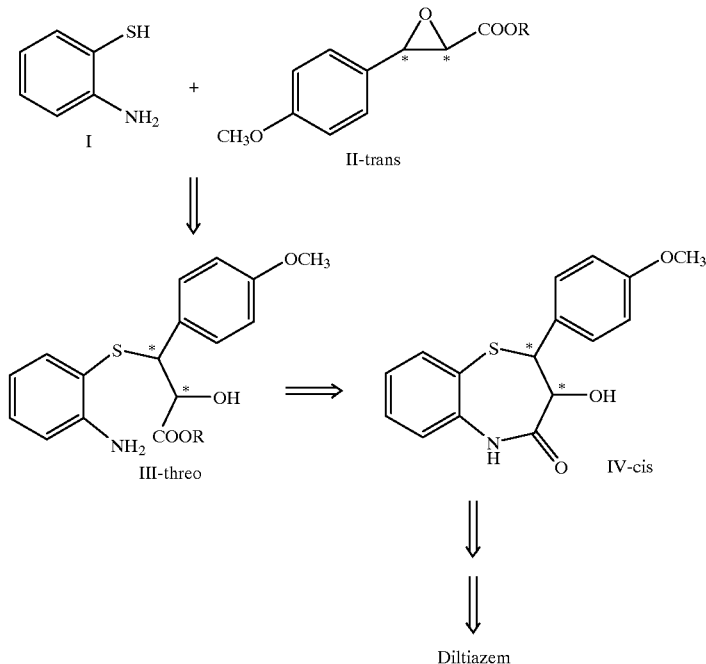

Scheme 1 wherein R is a hydrogen atom or a lower alkyl and the asterisks mark the stereogenic carbon atoms.

These methods use the compound of formula III-threo in racemic form, as intermediate. However, diltiazem shows stereocenters with S configuration and then, following the above reported scheme, a step for the separation of the (2S,3S) enantiomer from the (2R,3R) one is necessary.

The separation of the two enantiomers can be carried out on the intermediate (III) in the form of an ester (R=alkyl) as well as in the form of acid (R=H).

For example, the separation of the (2S,3S) and (2R,3R) enantiomers at the level of the ester III can be carried out by using an optically active acid as resolving agent (U.S. Pat. No. 5,144,025—Zambon Group S.p.A.) or by spontaneous resolution (U.S. Pat. No. 5,097,059—Zambon Group S.p.A.).

In case of separation at the level of the acid III, the methods described in the literature provide for, inter alia, the resolution with optically active bases such as α-phenylethylamine (European patent application 0 098 892—Tanabe Seiyaku Co. Ltd) or L-lysine (U.K. patent application 2130578—Istituto Luso Farmaco d'Italia S.p.A.) or the acylation in the presence of a lipase (European patent application 0 617 130—Orion-Yhtyma Oy Fermion).

It is evident that the resolution methods have the disadvantage of giving the desired (2S,3S) isomer with a maximum theoretical yield of 50% on the raceme and of giving also the corresponding (2R,3R) isomer, at the same time.

The isomers with (2R,3R) configuration, unsuitable for diltiazem synthesis, are then a waste product in the industrial synthesis.

As a consequence, a process for the recycle of said compounds in order to recover them for diltiazem synthesis should be useful.

As far as we know, the only method described in the literature for the recycle of an intermediate with (2R,3R) configuration is the process claimed in the U.S. Pat. No. 5,102,999 (Zambon Group S.p.A.) which provides for the racemization of the intermediate IV-cis (2R,3R).

We have now found a process for the conversion of the intermediates III-(2R,3R) to a mixture of enantiomers III-(2R,3R) and III-(2S,3S) which allows to re-use the enantiomers with (2R,3R) configuration of the intermediates of formula III for diltiazem synthesis.

Therefore, object of the present invention is a process for the conversion of threo-(2R,3R)-2-hydroxy-3-(2-aminophenylthio)-3-(4-methoxyphenyl)propionic acid derivatives of formula

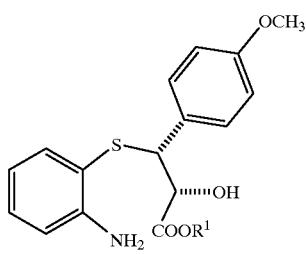

III-(2R,3R)

wherein R¹ is a linear or branched $C_1$–$C_3$ alkyl or a hydrogen atom;
into a mixture of enantiomers III-(2R,3R) and III-(2S,3S), comprising:
(a) the cyclization of the compound III-(2R,3R) to afford the corresponding compound of formula

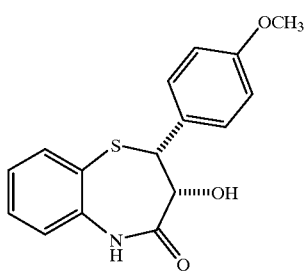

IV-(2R,3R)

(b) the conversion to the compound of formula

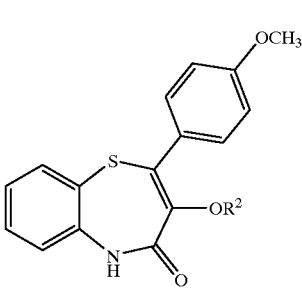

V wherein R² is a hydrogen atom or a $C_2$–$C_4$ acyl group,
(c) the reduction to afford the compound of formula

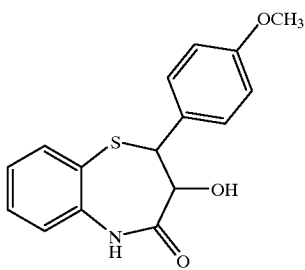

IV-cis (d) the opening reaction by treating with a strong acid or with a strong base in an alcoholic or aqueous solvent.

The mixture of the two enantiomers III-(2R,3R) and III-(2S,3S) obtained with the process object of the present invention can be resolved according to the already reported methods in order to separate the (2S, 3S) enantiomer useful for diltiazem synthesis.

In the present context, if not otherwise specified, the term mixture of enantiomers means a substantially racemic mixture (2R,3R:2S,3S ratio about 1:1) or a mixture wherein the enantiomer 2S,3S prevails.

Analogously, if the absolute configuration of the compounds of formula III or IV is not indicated, it means that said compounds are a substantially racemic mixture (2R, 3R:2S,3S ratio about 1:1) or a mixture wherein the enantiomer 2S,3 S prevails.

The term linear or branched $C_1$–$C_3$ alkyl means methyl, ethyl, propyl, isopropyl and the term $C_2$–$C_4$ acyl group means acetyl, propionyl, butyrl, isobutyrl.

The intermediates of formula III-(2R,3R) used as starting products in the process object of the present invention are known compounds and they are obtained as waste products in the optical separation processes for diltiazem synthesis.

Generally the compounds of formula III are in the form of acid (R¹=H) or in the form of methyl (R¹=CH₃) or ethyl (R¹=CH₂—CH₃) ester.

Preferably, in the process object of the present invention the compounds of formula III are methyl esters.

The cyclization of the compound III-(2R,3R) to afford the compound of formula IV-(2R,3R) can be carried out according to the known methods for the cyclization of the corresponding (2S,3S) enantiomer. For example, the cyclization of the esters of formula III-(2R,3R) can be carried out by treating with fosfonic acids (U.S. Pat. No. 5,223,612—Zambon Group S.p.A.) or by treating with sulfonic acids (European patent application 0 447 135—Tanabe Seiyaku Co. Ltd.). Similarly, the cyclization of the acid of formula III-(2R,3R) can be carried out by treating with sulfonic acids (European patent application 0 395 323—Tanabe Seiyaku Co. Ltd.) or with bases (European patent application 0 450 705—Stamicarbon B.V.).

In the process object of the present invention the cyclization reaction is preferably carried out starting from the methyl ester of formula III-(2R,3R) by treating with cis-propenyl-fosfonic acid.

The subsequent conversion reaction to the derivative V can be carried out according to known methods too. For example, the methods described in J. Org. Chem., 1996, 8586–8590 or in the already cited U.S. Pat. No. 5,102,999 can be used.

Preferably, in the process object of the present invention, the acetyl derivative of formula V (R²=COCH₃) is prepared, then hydrolysed to afford the compound Va which will be in equilibrium with its tautomer (Vb) as herein below reported.

Va ⇌ Vb

The subsequent reduction reaction allows to obtain the compound IV-cis.

Optionally, the hydrolysis and reduction reactions can be carried out one-pot, that is in an unique reaction environment, without isolating the compound Va (or Vb).

The preparation of the acetyl derivative V is preferably carried out by treating with acetic anhydride in dimethylsulfoxide, in the presence of catalytic amounts of pyridine. The optional hydrolysis can be then carried out by treating with bases such as sodium hydroxide or sodium mesylate.

The reduction of the compound of formula V can be carried out with known methods, for example by treating with hydrides according to what reported in the already cited U.S. Pat. No. 5,102,999.

The resultant compound IV-cis can be then converted into the corresponding compound of formula III-threo by treating with a strong acid or with a strong base in an alcoholic or aqueous solvent.

The amount of acid or base is at least equimolar, preferably in excess, with respect to the compound IV-cis.

Generally the reaction is carried out by using an excess of acid or base equal to 10%–30% in moles with respect to the compound IV.

The strong acids used in the process of the invention are inorganic acids such as hydrochloric, hydrobromic, sulfuric and fosforic acid or organic acids such as sulfonic acids, preferably methanesulfonic, p-toluenesulfonic and camphorsulfonic acid.

Sodium hydroxide is preferably used as strong base.

In the process object of the present invention methanesulfonic acid is preferably used.

The reaction is carried out in an alcoholic solvent such as, for example. methanol or ethanol, preferably in methanol, or in water optionally in admixture with a suitable co-solvent such as dimethylsulfoxide.

Dependently on the alcohol used as solvent the corresponding ester of formula III-threo is obtained which can then be used again in the preparation of diltiazem according to the synthetic route illustrated in the previous scheme 1.

When an aqueous solvent is used, the acid ($R^1$=H) of formula III-threo is obtained and used according to the synthetic route illustrated in scheme 1 too.

The opening reaction of the compound of formula IV-cis represents the most characterising feature of the process object of the present invention.

In fact, as far as we know, this reaction has never been described in the literature.

On the contrary, cyclizations of the compound III-threo to afford the compound IV-cis by using acids or bases have widely been described in the literature.

Furthermore, it is evident that the possibility of racemizing the waste products with (2R,3R) configuration of the process for diltiazem preparation at the level of one of the earliest synthetic intermediates represents a relevant advantage from a practical and economic viewpoint.

A particularly preferred embodiment of the process object of the present invention is the following.

The methyl ester of formula Ill-(2R,3R), obtained by resolution of the corresponding racemic mixture, is cyclized with cis-propenyl-fosfonic acid and then oxidised by treatment with acetic anhydride/dimethylsulfoxide/pyridine obtaining the acetyl derivative of formula V. After basic hydrolysis and reduction with sodium borohydride the racemic compound IV-cis is obtained and treated with an excess of methanesulfonic acid in methanol up to the obtainment of the racemic methyl ester III-threo.

The resolution of the racemic methyl ester III-threo allows to obtain the compound III-(2S,3S) which is used for diltiazem synthesis and the enantiomer III-(2R,3R) which can undergo a further recycle phase according to the process object of the present invention.

In order to better illustrate the present invention the following examples are now given.

EXAMPLE 1

A mixture of methyl (2R,3R)-2-hydroxy-3-(2-aminophenylthio)-3-(4-methoxyphenyl)-propionate (5 g; 15 mmoles) and cis-propenyl-fosfonic acid (0.183 g; 1.5 mmoles) in xylene (35 ml) was heated under reflux and stirring for 5.5 hours.

After distilling a xylene/methanol mixture (about 3%), the reaction mixture was cooled to 15° C.

The resultant precipitate was filtered under vacuum, washed with xylene (2×5 ml) and then dried in oven at 65° C. obtaining (2R,3R)-2,3-dihydro-3-hydroxy-2-(4-methoxyphenyl)-1,5-benzothiazepin-4(5H)-one (42 g; 89.6% yield).

EXAMPLE 2

A catalytic amount of pyridine (19.7 g; 0.25 moles) was added to a solution of (2R,3R)-2,3-dihydro-3-hydroxy-2-(4-methoxyphenyl)-1,5-benzothiazepin4(5H)-one (500 g; 1.66 moles) in dimethylsulfoxide (1100 g; 14.1 moles) and acetic anhydride (425 g; 4.17 moles). After keeping the solution under stirring at room temperature for 24 hours, water (1000 ml) was slowly added and the mixture was kept under stirring for 30 minutes.

The crystalline precipitate was filtered off, washed with methanol and dried obtaining 3-acetoxy-2-(4-methoxyphenyl)-1,5-benzothiazepin-4(5H)-one (481.6 g; 84.7% yield).

EXAMPLE 3

A suspension of 3-acetoxy-2-(4-methoxyphenyl)-1,5-benzothiazepin-4(5H)-one (17.1 g; 0.05 mmoles) in methanol (51 ml) was cooled in ice and then a solution of NaOH (5 g; 0.125 mmoles) in water (63 ml) was added.

The solution was then kept under stirring for 2 hours at room temperature.

After neutralisation with HCl 2N (50 ml) and extraction with ethyl acetate, the organic phase was washed twice with water, dried and concentrated obtaining a viscous oil.

The oil was treated with ethyl ether obtaining 2-(4-methoxyphenyl)-1,5-benzothiazepin-3,4(2H,5H)-dione (12.98 g; 86.7% yield) as a crystalline solid.

EXAMPLE 4

Sodium borohydride (0.567 g; 15 mmoles) was added to a solution of 2-(4-methoxyphenyl)-1,5-benzothiazepin-3,4 (2H,5H)-dione (4.25 g; 14.2 mmoles) in methanol (65 ml), kept under stirring, at 15° C.

After 1 hour the reaction mixture was poured into a buffer solution (100 ml) at pH 7 and methanol was removed by distillation under vacuum.

The resultant mixture was extracted with methylene chloride (2×30 ml).

After evaporation of the solvent under reduced pressure cis-2,3-dihydro-3-hydroxy-2-(4-methoxyphenyl)-1,5-benzothiazepin-4(5H)-one (4.15 g; 97% yield) as racemic mixture was obtained.

EXAMPLE 5

In a 500 ml flask, equipped with thermometer and condenser, cis-2,3-dihydro-3-hydroxy-2-(4-methoxyphenyl)-1,5-benzothiazepin-4(5H)-one (50 g; 165.9 mmoles) was suspended in methanol (200 ml) and methanesulfonic acid (19.2 g; 200 mmoles) was added to the mixture.

The reaction mixture was brought to reflux and the progress of the reaction was followed by TLC (eluent ethylacetate:hexane=6:4). After heating for 7 hours, the content of starting product was about 1%.

The reaction mixture was then cooled at room temperature before adding, with a dropping funnel, a 8% solution of sodium bicarbonate (208 g; final pH=7.0).

The resultant precipitate was filtered off and washed three times with water (3×50 ml). The resultant solid was then dried at 50° C. under vacuum up to constant weight obtaining methyl threo-2-hydroxy-3-(2-aminophenylthio)-3-(4-methoxyphenyl)-propionate (54 g; molar yield 94.2%; HPLC titre 96.5%).

EXAMPLE 6

30% Sodium methylate in methanol (0.1 ml; 0.5 mmoles) and, after 15 minutes, sodium borohydride (54 mg; 1.42 mmoles) were added to a suspension of 3-acetoxy-2-(4-methoxyphenyl)-1,5-benzothiazepin-4(5H)-one (1 g; 2.9 mmoles) in methanol (5 ml).

After keeping the mixture under stirring at room temperature for 5 hours, methanesulfonic acid (0.6 ml; 9.3 mmoles) was added and the mixture was heated under reflux for 5 hours. After cooling at room temperature, 8% sodium bicarbonate (9 ml) was added.

After adding toluene, the resultant solid was filtered off, washed with water (3×1 ml) and dried at 50° C. under vacuum obtaining methyl threo-2-hydroxy-3-(2-aminophenylthio)-3-(4-methoxyphenyl)propionate (0.92 g; molar yield 90%; HPLC titre 95%).

EXAMPLE 7

30% Sodium methylate in methanol (0.5 ml; 2.5 mmoles) and, after 15 minutes, sodium borohydride (0.28 g; 7.35 mmoles) were added to a suspension of 3-acetoxy-2-(4-methoxyphenyl)-1,5-benzothiazepin-4(5H)-one (5 g; 14.7 mmoles) in methanol (25 ml).

After keeping the mixture under stirring at room temperature for 5 hours, a 6.5M solution of hydrochloric acid in methanol (2.7 ml; 17.6 mmoles) was added and the mixture was heated under reflux for 5 hours.

After cooling at room temperature, 8% sodium bicarbonate (16 ml) was added.

The resultant precipitate was filtered off, washed with water (3×5 ml) and dried at 50° C. under vacuum obtaining methyl threo-2-hydroxy-3-(2-aminophenylthio)-3-(4-methoxyphenyl)-propionate (5 g; molar yield 85%; $^1$H-NMR titre 75%).

What is claimed is:

1. A process for the conversion of threo-(2R,3R)-2-hydroxy-3-(2-aminophenylthio)-3-(4-methoxyphenyl) propionic acid derivatives of formula

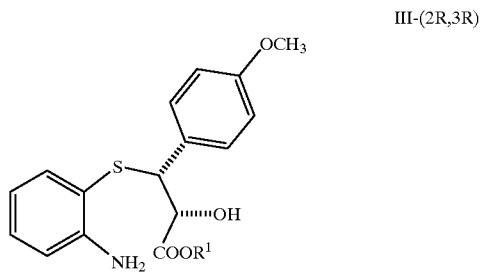

III-(2R,3R)

wherein $R^1$ is a linear or branched $C_1$–$C_3$ alkyl or a hydrogen atom;

into a mixture of enantiomers III-(2R,3R) and III-(2S,3S), comprising:

(a) the cyclization of the compound III-(2R,3R) to afford the corresponding compound of formula

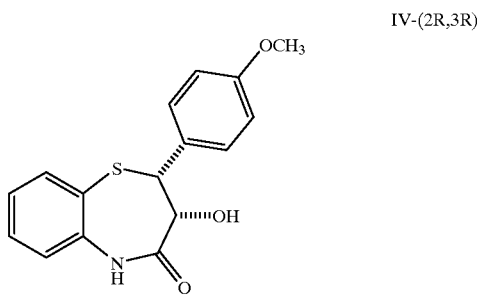

IV-(2R,3R)

(b) the conversion to the compound of formula

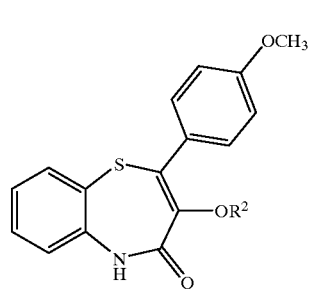

V wherein $R^2$ is a hydrogen atom or a $C_2$–$C_4$ acyl group, (c) the reduction to afford the compound of formula

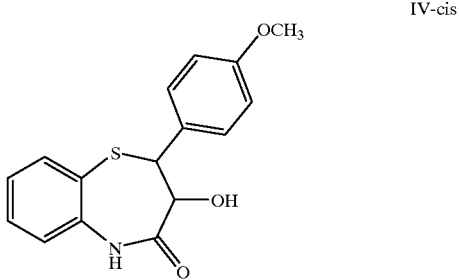

IV-cis (d) the opening reaction by treating with a strong acid or with a strong base in an alcoholic or aqueous solvent.

2. A process according to claim 1 for the conversion of the methyl ester of threo-(2R,3R)-2-hydroxy-3-(2-aminophenylthio)-3-(4-methoxyphenyl)-propionic acid.

3. A process according to claim 1 wherein the compound of formula V wherein $R^2$ is acetyl is used.

4. A process according to claim 1 wherein the opening reaction is carried out by treating with a strong acid.

5. A process according to claim 4 wherein the strong acid is selected from the group consisting of hydrochloric, hydrobromic, sulfuric, fosforic, methanesulfonic, p-toluenesulfonic and camphorsulfonic acid.

6. A process according to claim 5 wherein the strong acid is methanesulfonic acid.

7. A process according to claim 4 wherein an alcoholic solvent is used.

8. A process according to claim 7 wherein the solvent is methanol.

9. A method for the preparation of diltiazem, the method comprising conducting the process according to claim 1 and thereafter synthesizing the diltiazem from the III-(2S,3S) enantiomer obtained in the process.

* * * * *